US012290300B1

(12) United States Patent
Pedicini

(10) Patent No.: US 12,290,300 B1
(45) Date of Patent: May 6, 2025

(54) ORTHOPEDIC IMPACTOR TOOL

(71) Applicant: Fidelis Partners, LLC, Cheyenne, WY (US)

(72) Inventor: Christopher Pedicini, Brentwood, TN (US)

(73) Assignee: FIDELIS PARTNERS, LLC, Cheyenne, WY (US)

( * ) Notice: Subject to any disclaimer, the term of this patent is extended or adjusted under 35 U.S.C. 154(b) by 0 days.

(21) Appl. No.: 18/889,589

(22) Filed: Sep. 19, 2024

Related U.S. Application Data

(60) Provisional application No. 63/609,034, filed on Dec. 12, 2023.

(51) Int. Cl.
*A61B 17/92* (2006.01)

(52) U.S. Cl.
CPC .................................... *A61B 17/92* (2013.01)

(58) Field of Classification Search
CPC . A61B 17/92; A61B 17/921; A61B 2017/922; A61B 2017/924; A61B 2017/925; A61B 2017/927; A61B 2017/928
See application file for complete search history.

(56) References Cited

U.S. PATENT DOCUMENTS

| | | | |
|---|---|---|---|
| 6,520,266 B2 * | 2/2003 | Bongers-Ambrosius | B25D 11/12 173/2 |
| 6,868,918 B2 * | 3/2005 | Shinohara | B23Q 5/027 30/392 |
| 10,342,591 B2 * | 7/2019 | Pedicini | B25D 11/068 |
| 11,013,503 B2 * | 5/2021 | Pedicini | A61B 17/92 |
| 11,696,770 B2 * | 7/2023 | Pedicini | A61B 90/30 606/79 |
| 12,004,793 B2 * | 6/2024 | Levy | A61B 17/92 |
| 12,029,406 B2 * | 7/2024 | Pedicini | A61F 2/4607 |
| 12,064,158 B2 * | 8/2024 | Marinkovich | A61B 17/92 |
| 12,070,256 B2 * | 8/2024 | Slocum | A61B 17/92 |
| 12,121,279 B2 * | 10/2024 | Pedicini | A61B 17/92 |
| 2011/0064978 A1 * | 3/2011 | McGahan | H01M 50/213 429/61 |
| 2016/0199199 A1 * | 7/2016 | Pedicini | A61B 17/92 606/100 |
| 2017/0100829 A1 * | 4/2017 | Pedicini | B25C 1/047 |
| 2018/0055518 A1 * | 3/2018 | Pedicini | A61B 17/17 |
| 2018/0055552 A1 * | 3/2018 | Pedicini | A61B 17/92 |
| 2019/0183554 A1 * | 6/2019 | Pedicini | A61F 2/4612 |
| 2022/0142693 A1 * | 5/2022 | Slocum | A61B 17/92 |

(Continued)

*Primary Examiner* — Eric S Gibson
(74) *Attorney, Agent, or Firm* — XSENSUS LLP

(57) ABSTRACT

An orthopedic impactor tool may include a motor, a linear motion converter operatively coupled to the motor, a thrown mass operatively coupled to the linear motion converter, and an anvil including a at least one impact surface. During an operational cycle of the orthopedic impactor tool, the motor may generate rotational motion that drives the linear motion converter. The linear motion converter may, while being driven by the rotational motion, convert the rotational motion into linear motion and communicate the linear motion to the thrown mass. The linear motion, communicated to the thrown mass, causes the thrown mass to accelerate and impact the at least one impact surface imparting a linear impact force on the anvil. The motor and the linear motion converter may operate on independent axes.

19 Claims, 9 Drawing Sheets

(56) References Cited

U.S. PATENT DOCUMENTS

| | | | |
|---|---|---|---|
| 2022/0226033 A1* | 7/2022 | Slocum | A61B 17/92 |
| 2022/0240947 A1* | 8/2022 | Marinkovich | A61B 17/1628 |
| 2022/0273317 A1* | 9/2022 | Levy | A61B 17/92 |

* cited by examiner

ORTHOPEDIC IMPACTOR TOOL

CROSS-REFERENCE TO RELATED APPLICATION

This application claims the benefit of U.S. Provisional Application No. 63/609,034, filed Dec. 12, 2023, which is incorporated herein by reference in its entirety.

BACKGROUND

Impactor tools are designed to deliver an impact force to a target object or material. The impactor tools are commonly used in various industries and applications where precise and controlled force is required to perform tasks, such as fastening, shaping, breaking, and/or compacting tasks.

SUMMARY

Some implementations described herein relate to an orthopedic impactor tool, comprising: a motor; a linear motion converter operatively coupled to the motor; a thrown mass operatively coupled to the linear motion converter; and an anvil including at least one impact surface; wherein, during an operational cycle of the orthopedic impactor tool, the motor generates rotational motion that drives the linear motion converter, wherein the linear motion converter, while being driven by the rotational motion, converts the rotational motion into linear motion and communicates the linear motion to the thrown mass, wherein the linear motion, communicated to the thrown mass, causes the thrown mass to accelerate and impact the at least one impact surface imparting a linear impact force on the anvil, and wherein the motor and the linear motion converter operate on independent axes.

Some implementations described herein relate to an orthopedic impactor tool, comprising: a motor; a linear motion converter operatively coupled to the motor; a thrown mass operatively coupled to the linear motion converter; and an anvil including at least one impact surface; wherein, during an operational cycle of the orthopedic impactor tool, the motor generates rotational motion that drives the linear motion converter, wherein the linear motion converter, while being driven by the rotational motion, converts the rotational motion into linear motion and communicates the linear motion to the thrown mass, wherein the linear motion, communicated to the thrown mass, causes the thrown mass to accelerate towards the at least one impact surface of the anvil, and wherein the motor at least one of coasts, or operates a reduced motor power, before the thrown mass imparts a linear impact on the at least one impact surface of the anvil.

Some implementations described herein relate to a method of operating an orthopedic impactor tool, the method including: causing, by a controller of the orthopedic impactor tool, a motor of the orthopedic impactor tool to generate rotational motion that drives a linear motion converter of the orthopedic impactor tool, wherein the linear motion converter, while being driven by the rotational motion, converts the rotational motion into linear motion and communicates the linear motion to a thrown mass of the orthopedic impactor tool, wherein the linear motion, communicated to the thrown mass, causes the thrown mass to accelerate and impact at least one impact surface of an anvil of the orthopedic impactor tool imparting a linear impact force on the anvil, and wherein the motor and the linear motion converter operate on independent axes.

DETAILED DESCRIPTION OF EXAMPLE EMBODIMENTS

Figure 1A:
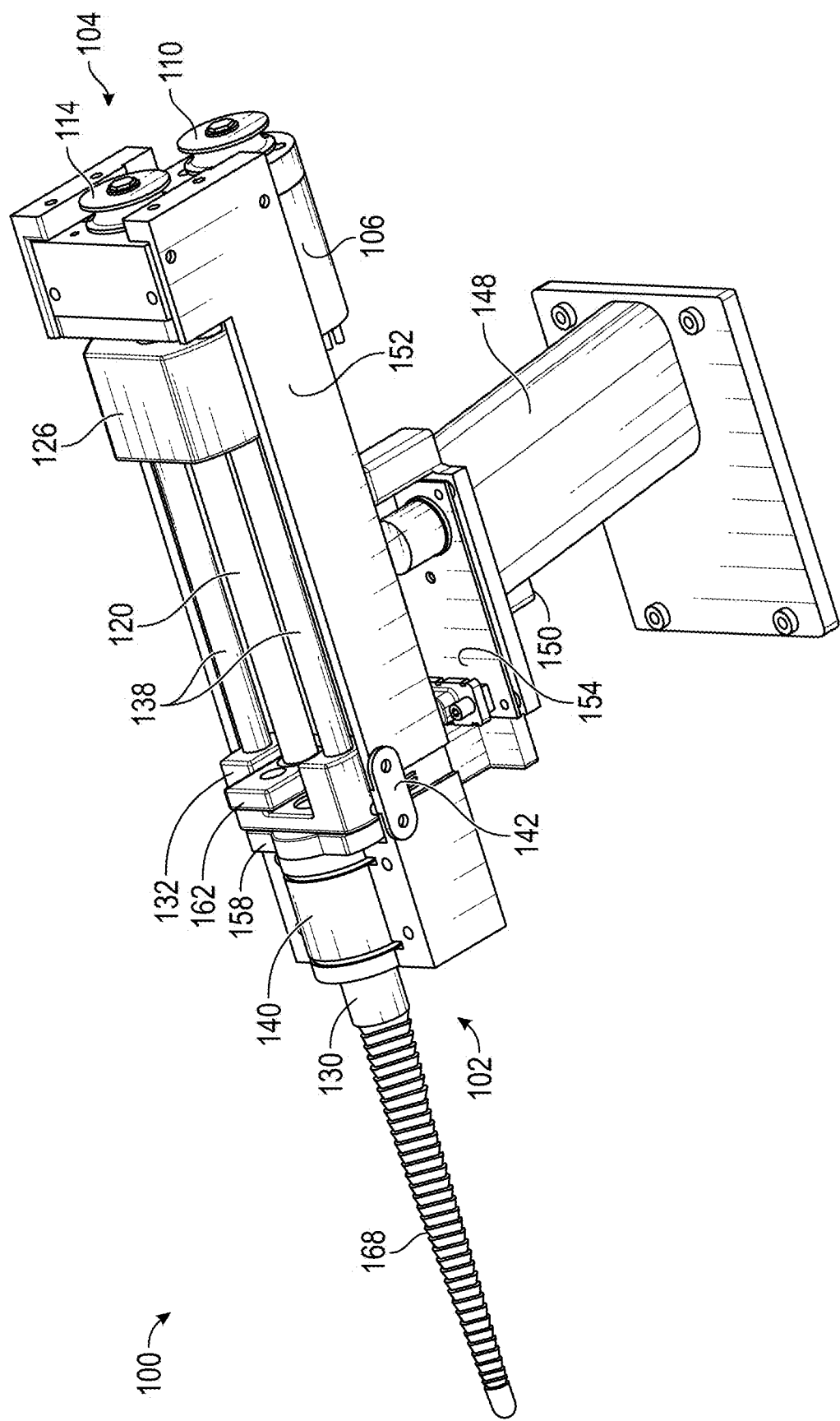
FIGS. 1A-1G are diagrams of an example orthopedic impactor tool, in accordance with some embodiments of the present disclosure.
Figure 1B:
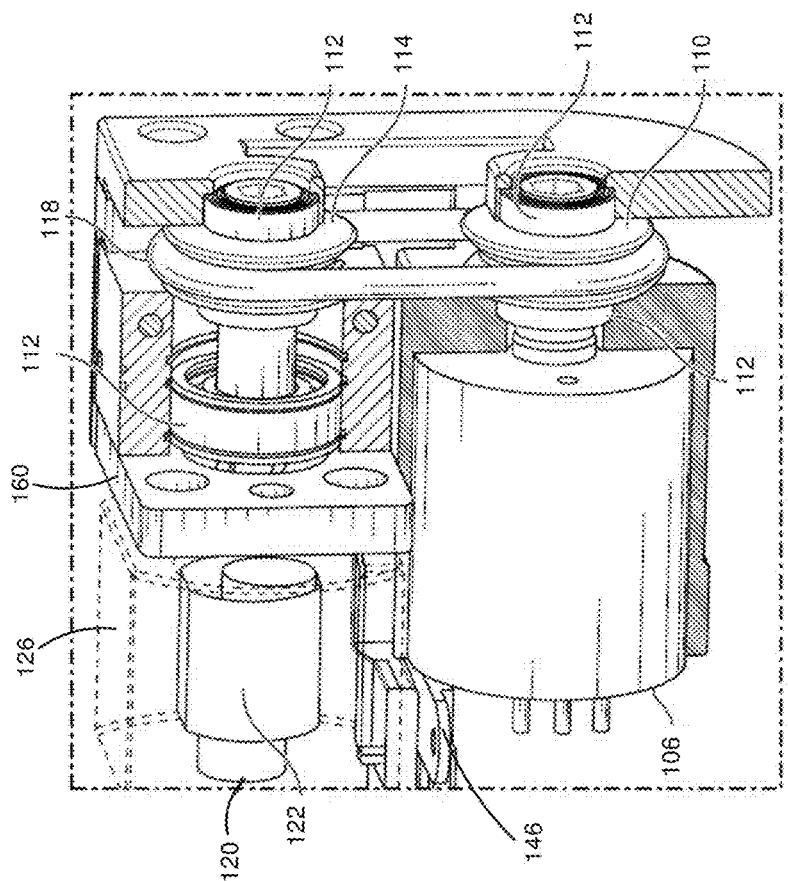

The following detailed description of example implementations refers to the accompanying drawings. The same reference numbers in different drawings may identify the same or similar elements.

In the field of orthopedics, prosthetic devices, such as artificial joints, are often implanted or seated in a bone cavity of a patient. The bone cavity must be created before the prosthesis is seated or implanted, and, traditionally, a surgeon removes worn, excess, or diseased bone structure from an implant area in which the bone cavity will be formed, and then drills and hollows out the bone cavity (e.g., a bone cavity along a medullary canal of a bone of the patient). A prosthesis usually includes a stem, or other protrusion, that is inserted into the bone cavity.

To create such a bone cavity, high energy linear forces are required to impart high energy linear impacts onto one or more surgical tools. A typical technique that the surgeon uses is manually hammering a broach (e.g., a cutting tool that conforms to a shape of the stem of the prosthesis) into the implant area using a mallet. However, this manual approach presents challenges and problems, such as being imprecise, leading to unnecessary mechanical stress on the bone of the patient, and producing unsatisfactory results (e.g., a location and configuration of the bone cavity are inaccurate). Additionally, this manual approach requires the surgeon to expend significant energy creating the high energy linear forces that are required to impart the high energy linear impacts onto the broach, leading to fatigue of the surgeon.

In some cases, the surgeon uses a powered impactor tool for orthopedic operations that require high energy linear impacts. However, typical powered impactor tools have disadvantages and drawbacks, such as inefficiently communicating energy necessary to provide the high energy linear impacts (e.g., inefficiently converting rotational motional into linear motion to cause a thrown mass to move and strike an impact surface of an anvil), inadequate robustness (e.g., typical powered impactor tools include a relatively high number of components that wear easily and have a short life), complex and expensive construction, and having a large size and/or weight which impedes maneuverability and access to the surgical site.

For example, typical powered impactor tools include a power launch spring, a thrown mass, and an anvil. To provide an impact force, the power launch spring is released from a compressed state converting potential energy, stored in the power launch spring, to kinetic energy. The power launch spring transmits the kinetic energy to the thrown mass, resulting in an acceleration of the thrown mass from an initial position toward the anvil. After the thrown mass impacts the anvil, the power launch spring retracts and returns the anvil to the initial position.

However, when the power launch spring is used to launch the thrown mass, typical energy conversion efficiencies are less than 50%. Furthermore, the repetitive launching and retracting of the power launch spring during each operational cycle can lead to material fatigue causing reduced elasticity and increased wear in one or more components of the typical powered impactor tools and audible harmonics do to spring cycling.

Additionally, typical powered impactor tools inefficiently use a clutch and/or an energy storage device (e.g., a flywheel) to communicate linear motion to the thrown mass (e.g., typical powered impactor tools inefficiently convert rotational motion to linear motion). For example, if the thrown mass is coupled to a linear motion converter, then the clutch is used to engage the flywheel, which is powered by the motor, to the linear motion converter to convert rotational motion (e.g., generated by the flywheel) into the linear motion that causes the thrown mass to linearly move. Accordingly, each component (e.g., the motor, the energy storage device, the clutch, the linear motion converter, and the thrown mass) introduces potential failure points, which decreases robustness and increases cost of such typical powered impactor tools.

Furthermore, typical powered impactor tools have shown issues with handling axial forces communicated to an actuator (e.g., a drive motor) of the typical powered impactor tools. As an example, typical powered impactor tools cannot sufficiently mitigate axial forces (e.g., generated by high energy linear impacts provided by the typical powered impactor tools) such that the drive motor is damaged and/or rendered inoperable, reducing the life of the typical powered impactor tools and inhibiting their application in robotic surgery due to excessive recoil.

Some implementations described herein provide an orthopedic impactor tool (e.g., an improved electrically driven orthopedic impactor tool). The orthopedic impactor tool of the present disclosure communicates energy necessary to provide high energy linear impacts more efficiently, with increased robustness, lower cost of construction, reduced recoil and noise compared to typical powered impactor tools, as described in more detail elsewhere herein.

As an example, some implementations described herein provide an orthopedic impactor tool has an energy conversion efficiency of at least approximately 70% (e.g., the orthopedic impactor tool converts rotational motion to linear motion at an energy conversion efficiency of at least approximately 70%), which was an unexpected discovery, compared to an energy conversion efficiency of less than 50% for typical powered impactor tools. As another example, the orthopedic impactor tool uses a reduced number of components to communicate the linear motion necessary to provide the high energy linear impacts relative to a number of components that are used to by the powered impactor tools. This allows a size and cost of the orthopedic impactor tool to be significantly reduced relative to a size of typical powered impactor tools. Additionally, this enables a robustness of the orthopedic impactor tool to be greater than a robustness of typical impactor tools.

As another example, some implementations described herein provide an orthopedic impactor tool that mitigates axial forces communicated to an actuator (e.g., a motor, among other examples) of the orthopedic impactor tool. For example, the orthopedic impactor tool may use an off-axis drive mechanism to mitigate axial forces communicated to the actuator, as described in more detail elsewhere herein. As an example, the off-axis drive mechanism may use a coupling drive assembly (e.g., a flexible coupling drive assembly, among other examples) having a drive-axis that is independent (or separate) from an impact axis.

It was unexpectedly discovered that by using a drive axis and an impact axis that are independent from one another, a length of the orthopedic impactor tool is substantially reduced compared to a length of typical powered impactor tools. Additionally, using a coupling drive assembly, which enables the drive axis to be on a different axis than the impact axis is beneficial because reactionary shock associated with linear impacts (e.g., high energy linear impacts, among other examples) cannot be transmitted to the actuator (e.g., because the actuator is shielded from all shock associated with the linear impacts).

In some implementations, the coupling drive assembly may use a coupling element (e.g., a flexible coupling element, among other examples) to transfer rotational energy from the actuator to an output drive assembly via a linear motion converter. One or more parameters of the coupling element may be optimized to avoid torque overload on the actuator. For example, a slip torque parameter of the coupling element may be optimized such that the coupling element slips when the torque load applied to the orthopedic impactor tool meets, or exceeds, a slippage torque (e.g., a threshold slip torque value, such as a threshold slip torque value of at least four inch-pounds (in-lbs), among other examples), as described in more detail elsewhere herein. Additionally, or alternatively, the slippage torque may correspond to a linear force (e.g., a maximum linear force) communicated from the actuator to the linear motion converter. For example, the slippage torque may correspond to a maximum linear force communicated from the actuator to the linear motion converter of less than approximately thirty pounds. In other words, if the actuator communicates more than a thirty pound thrust force, in a linear direction, when the linear motion converter is stopped, slippage occurs between a drive coupling of the actuator to the linear motion converter.

Accordingly, in some implementations, the orthopedic impactor tool is designed to be used for orthopedic operations requiring high energy linear impacts. For example, a surgeon may use the orthopedic impactor tool, in conjunction with a broach, to perform a femoral broaching procedure when preparing a femoral canal for insertion of an artificial implant or prosthesis. As another example, the surgeon may use the orthopedic impactor tool for artificial implant or prosthesis positioning (e.g., to set the artificial implant or prosthesis in place). As a still further example, the surgeon may use the orthopedic impactor tool to drive or remove orthopedic nails. Although the orthopedic impactor tool has been described as being designed for use in performing orthopedic operations requiring high energy linear impacts, the orthopedic impactor tool may be used in association with any suitable applications, such as any suitable surgical applications that require high energy linear impacts (e.g., osteotomes, among other examples).

FIGS. 1A-1G are diagrams of an example orthopedic impactor tool 100 that may be used to provide high energy linear impacts (e.g., in association with orthopedic procedures, among other examples). As shown in FIGS. 1A-1G, the orthopedic impactor tool 100 includes a front end 102 opposite a rear end 104, an actuator (e.g., a motor 106), a drive pulley 110, a driven pulley 114, a coupling element (e.g., a belt 118), a linear motion converter (e.g., a lead screw 120 and a lead nut 122 operatively coupled to a thrown mass 126), an impact element (e.g., an anvil 130), an anvil anti-rotation element 132, a forward impact surface 134, a rearward impact surface 136, reverse impact rods 138 (e.g., which also function as guiding rods), an anvil guide bushing 140, one or more sensors (e.g., a first sensor 142, a second sensor 144, and a third sensor 146), a handle 148, a trigger mechanism 150, an enclosure 152, a controller 154, a detent element 156, a first impact absorbing mechanism 158, a second impact absorbing mechanism 160, and an axial support mechanism 162.

The motor 106 is mechanically coupled to the drive pulley 110 (e.g., via a retaining compound, among other examples). The drive pulley 110 is mechanically coupled to the driven pulley 114 via the belt 118. The driven pulley 114 is mechanically coupled to the lead screw 120, which is operatively coupled to the thrown mass 126 (e.g., via a lead nut, as described in more detail elsewhere herein). In some implementations, the orthopedic impactor tool 100 may include bearings 112 that support one or more components of the orthopedic impactor tool 100 (e.g., the bearings 112 may support the motor 106, the drive pulley 110, the driven pulley 114 and/or the lead screw 120, among other examples).

Figure 1C:
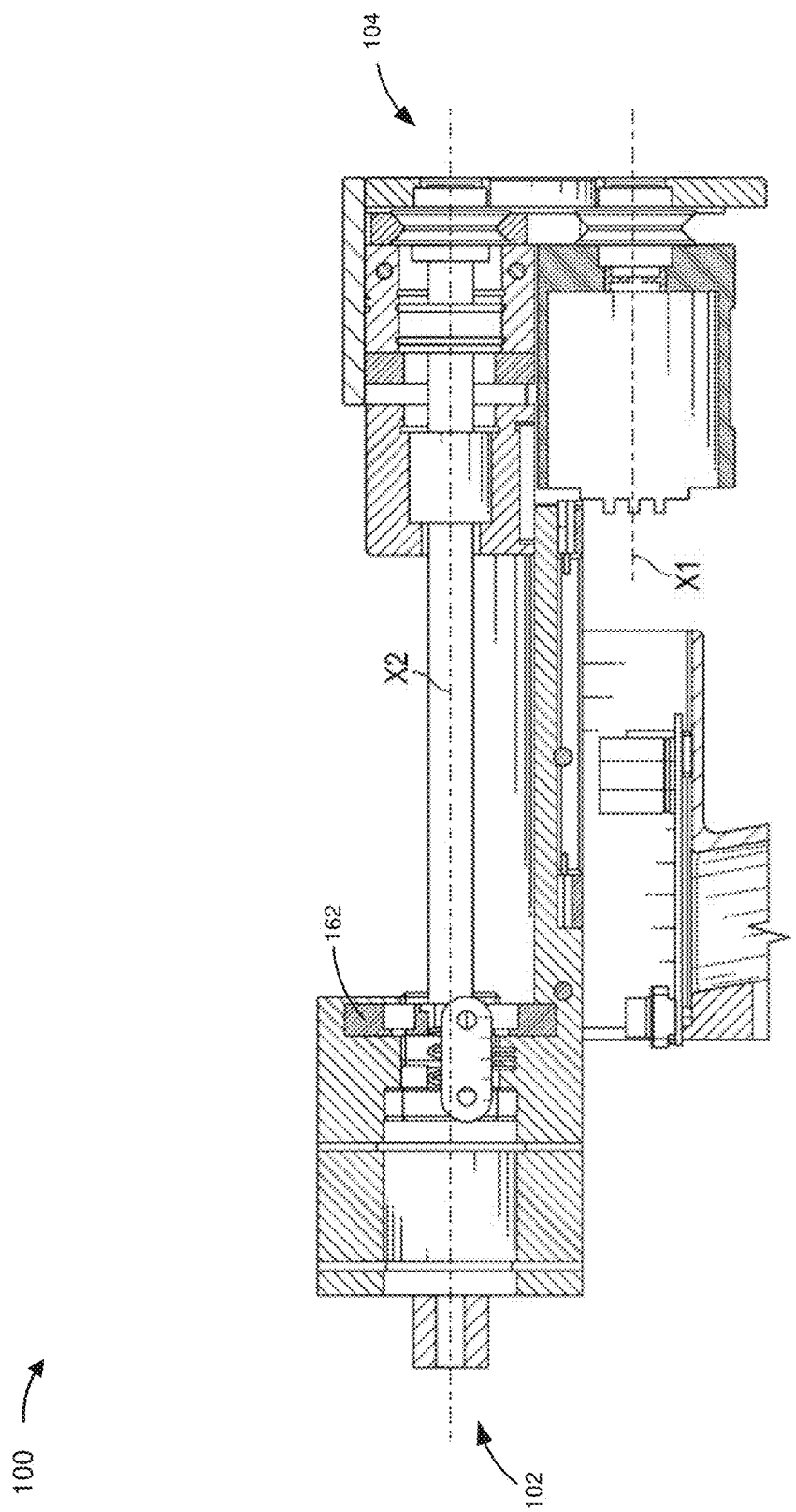
Figure 1D:
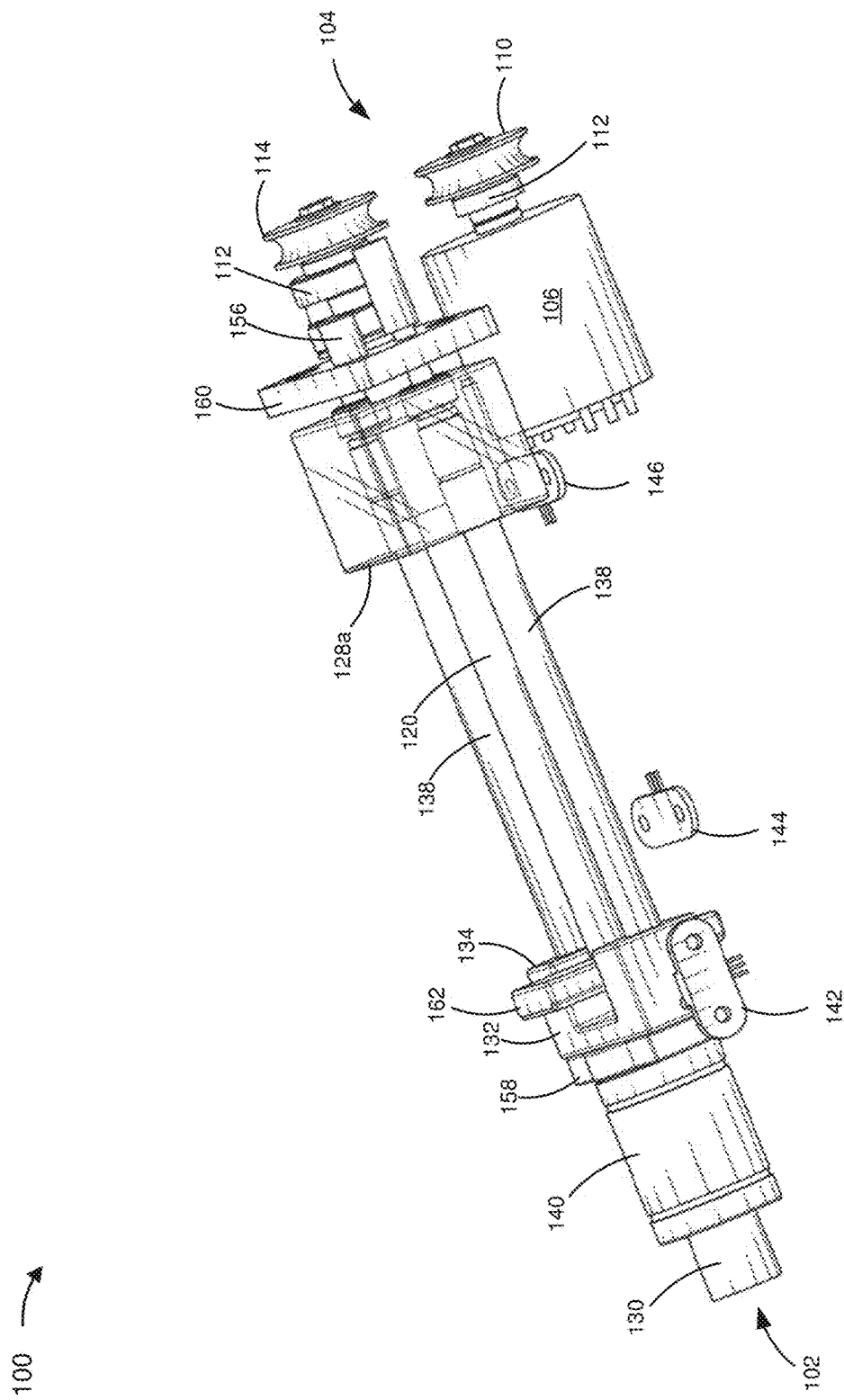
Figure 1E:
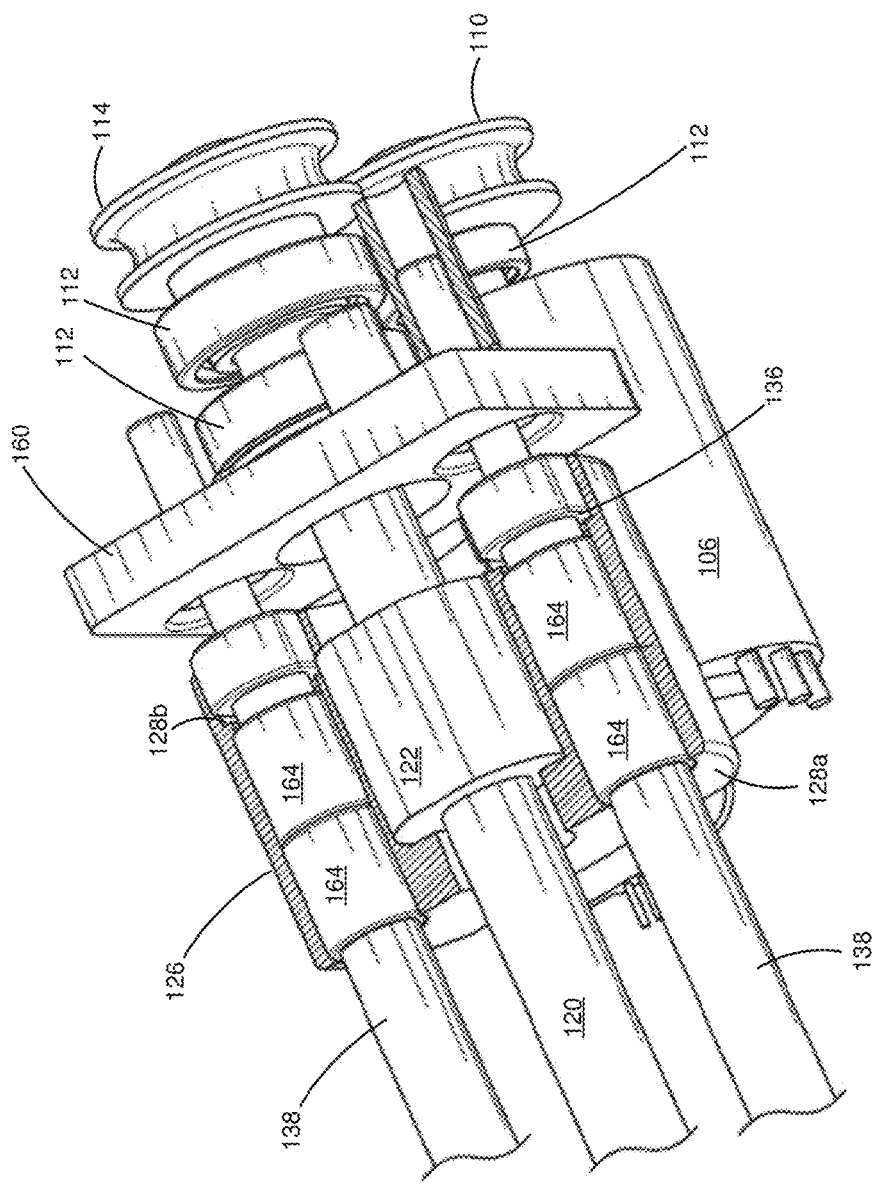
Figure 1F:
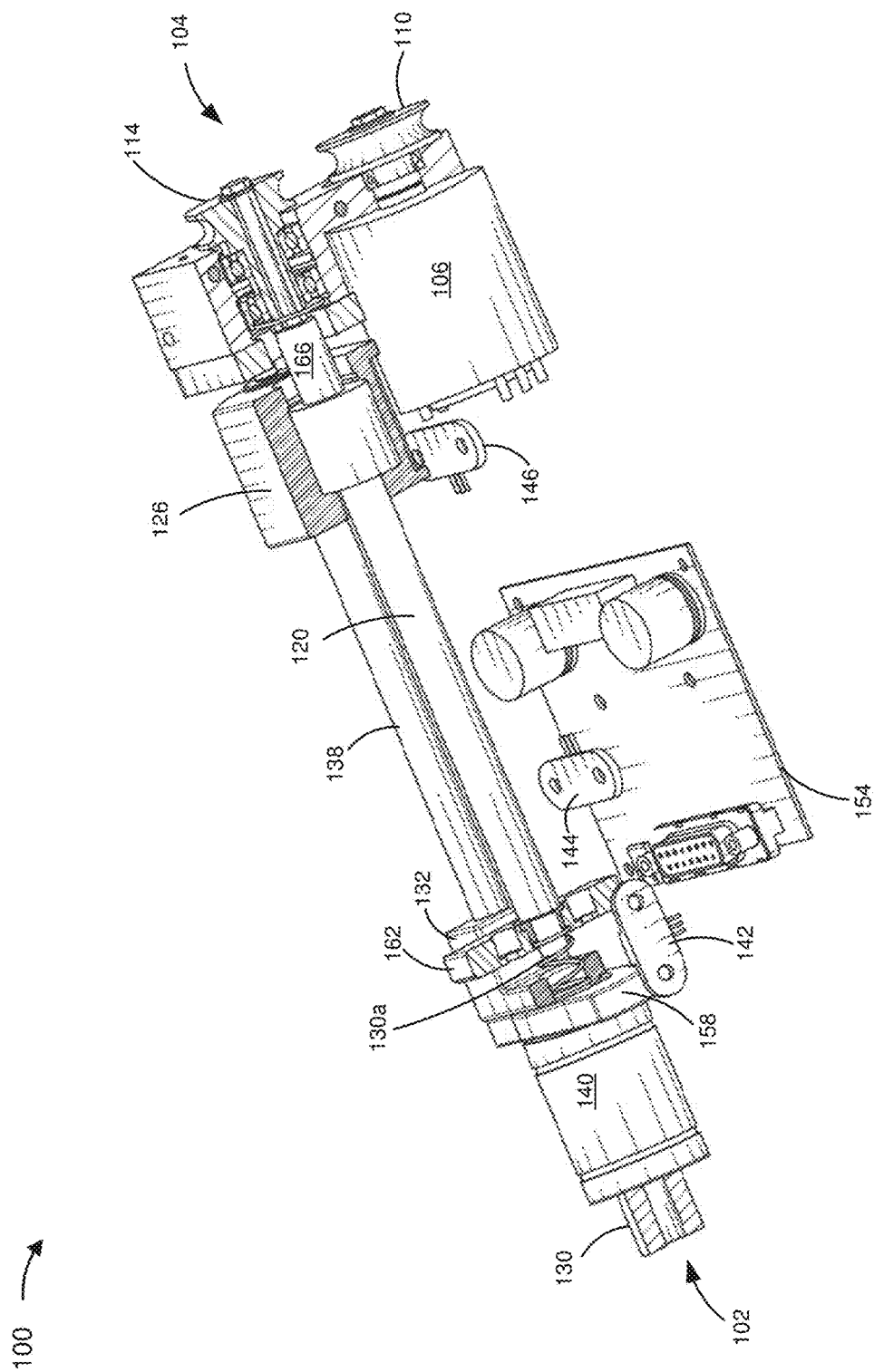
Figure 1G:
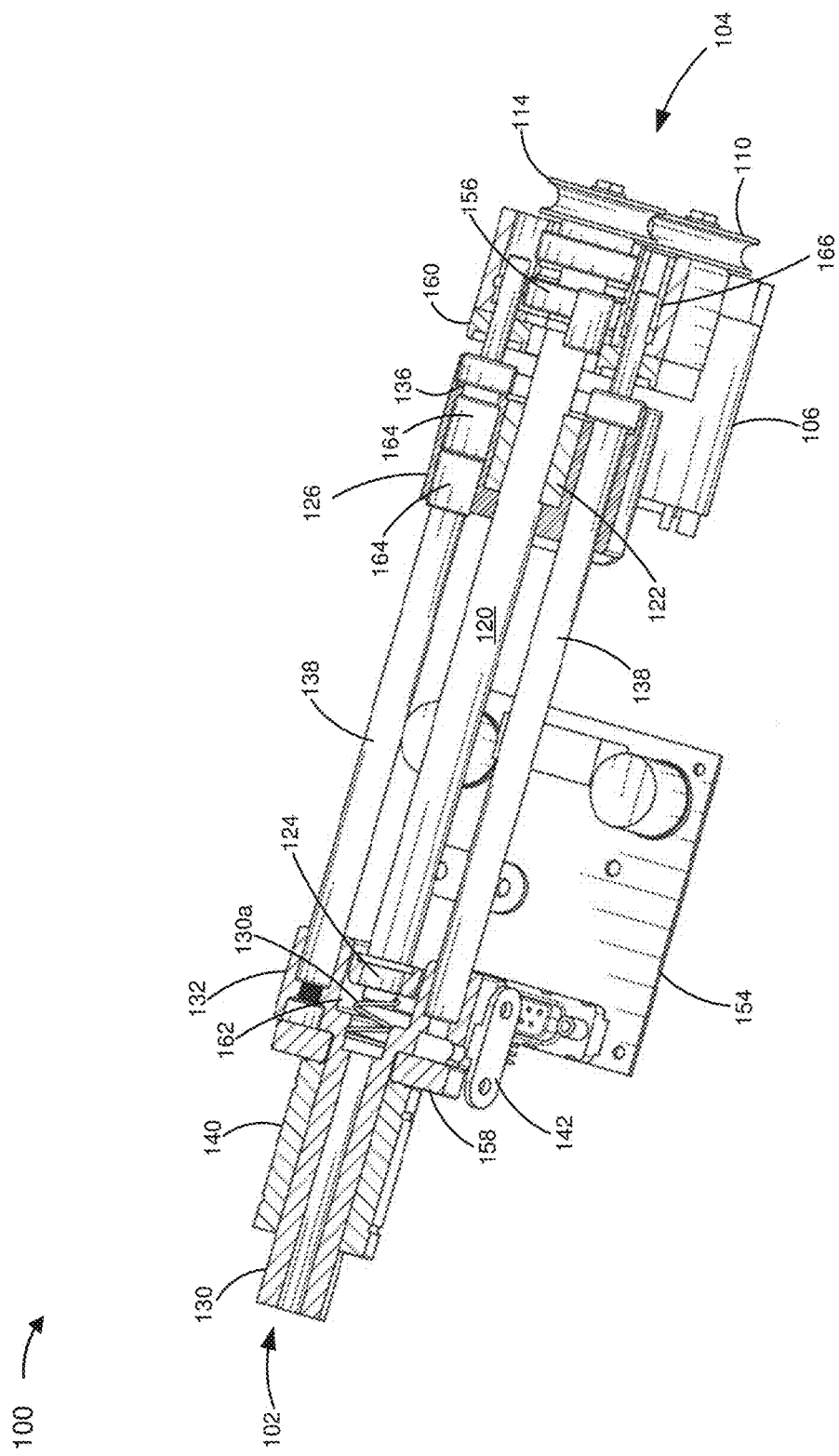

Thus, in some implementations, the motor 106 is positioned such that the motor 106 operates along a drive axis (e.g., shown as a drive axis X1 in FIG. 1C) and the lead screw 120 operates along an impact axis (e.g., shown as an impact axis X2 in FIG. 1C). The motor 106 generates rotational energy along the drive axis X1, which causes the drive pulley 110 to rotate. The belt 118 transmits rotational motion from the drive pulley 110 to the driven pulley 114. The lead screw 120 converts rotational energy from the driven pulley 114 to linear motion causing the thrown mass 126 to travel linearly in a direction along the impact axis X2 (e.g., to provide an impact force, such as an impact force to one or more impact surfaces of the anvil 130, as described in more detail elsewhere herein).

Accordingly, for example, the motor 106 generates rotational motion that drives the lead screw 120. As an example, the motor 106 may generate forward rotational motion that causes forward rotation of the lead screw 120, which, in turn, causes the lead nut 122 to move linearly along a shaft of the lead screw 120 (e.g., the lead nut 122 translates along the shaft of the lead screw 120) in a forward direction (e.g., toward the front end 102 of the orthopedic impactor tool 100 and away from the motor 106). As another example, the motor 106 may generate reverse rotational motion that causes reverse rotation of the lead screw, which, in turn, causes the lead nut 122 to move linearly along a shaft of the lead screw 120 (e.g., the lead nut 122 translates along the shaft of the lead screw 120) in a rearward direction (e.g., toward the rear end 104 of the orthopedic impactor tool 100 and toward the motor 106).

In some implementations, the coupling element (e.g., the belt 118) may be an elastomer that may slip at a threshold slip torque value. This elastomer may be made of silicone, nitrile butadiene rubber (NBR), and/or fluoroelastomer (FKM), among other examples. As an example, the coupling element may slip when a torque load applied to the linear motion converter exceeds a threshold slip torque value (e.g., a threshold slip torque value of at least four inch-pounds (in-lbs), among other examples), preventing damage to the actuator.

Accordingly, one or more parameters associated with the coupling element (e.g., one or more material parameters and/or slip torque parameters, among other examples) may be optimized to avoid torque overload on the actuator. In some implementations, the orthopedic impactor tool 100 may include an additional decoupling mechanism that decouples the actuator from receiving overload torque. For example, the orthopedic impactor tool 100 may include a slip clutch mechanism (e.g., provided between the actuator and the linear motion converter) that decouples the actuator from receiving overload torque. As an example, the slip clutch mechanism may be a mechanical slip clutch (e.g., a friction disk), a magnetic slip clutch, and/or an electrical slip clutch, among other examples.

In some implementations, the coupling element may be matingly coupled to rotary motion transfer elements included in the set of rotary motion transfer elements (e.g., the drive pulley 110 and the driven pulley 114). As an example, the drive pulley 110 and the driven pulley 114 may include grooves, and the belt 118 may include ribs. The grooves of the drive pulley 110 and the driven pulley 114 may interface with the ribs of the belt 118 (e.g., to provide an interlocking connection).

Furthermore, although the coupling element is shown as the belt 118 having a circular cross-section, the coupling element may be any suitable coupling element having any suitable cross-section and/or profile (e.g., a trapezoidal cross-section and/or an X-shaped profile, among other examples). Additionally, although the set of rotary motion transfer elements is shown and described as including the drive pulley 110, the bearings 112, and the driven pulley 114, the set of rotary motion transfer elements may include any suitable type of rotary motion transfer elements and/or any suitable number of rotary motion transfer elements.

In this way, because the orthopedic impactor tool 100 uses a drive axis (e.g., the drive axis X1) and an impact axis (e.g., the impact axis X2) that are independent from one another (e.g., that operate on independent axes), a length of the orthopedic impactor tool 100 is substantially reduced compared to a length of typical powered impactor tools. Additionally, using the coupling drive assembly, which enables the drive axis to be on a different axis than the impact axis, is beneficial because reactionary shock associated with linear impacts (e.g., high energy linear impacts, among other examples) is not transmitted to the actuator (e.g., the motor 106) through the linear motion converter because the actuator is not collinearly aligned with the linear motion converter and is thus shielded from virtually all shock associated with the linear impacts. Isolation of the actuator (e.g., the motor 106) from the shock coupled through the linear motion converter by using two separate axes unexpectedly increased a longevity of the orthopedic impactor tool 100 while also reducing the overall length of the orthopedic impactor tool 100 relative to typical powered impactor tools.

In some implementations, compliant mechanisms, such as spider couplings positioned between the shaft of the motor 106 and the linear motion converter, may be used to isolate one or more components of the orthopedic impactor tool 100. As an example, a spider coupling may be used to reduce loading to the actuator (e.g., the motor 106) from an output shock. Additionally, or alternatively, a spline and a spline nut may be used to reduce shock loads transmitted from the linear motion converter to the actuator (e.g., the motor 106).

The motor 106 generates rotational motion that drives the lead screw 120 and the lead nut 122. As an example, the motor 106 may generate forward rotational motion that causes forward rotation of the lead screw, which, in turn, causes the lead nut 122 to move linearly along a shaft of the lead screw 120 (e.g., the lead nut 122 translates along the shaft of the lead screw 120) in a forward direction (e.g., toward the front end 102 of the orthopedic impactor tool 100). As another example, the motor 106 may generate reverse rotational motion that causes reverse rotation of the lead screw 120, which, in turn, causes the lead nut 122 to move linearly along a shaft of the lead screw 120 (e.g., the lead nut 122 translates along the shaft of the lead screw 120) in a rearward direction (e.g., toward the rear end 104 of the orthopedic impactor tool 100).

The thrown mass 126 is fixedly connected to the lead nut 122. Because the thrown mass 126 is fixedly connected to the lead nut 122, the thrown mass 126 moves linearly with the lead nut 122 (e.g., as the lead nut 122 translates along the shaft of the lead screw 120, the thrown mass 126 translates with the lead nut 122). The thrown mass 126 includes a forward striking surface 128a (e.g., for providing a forward linear impact force on the anvil 130) and a rearward striking surface 128b (e.g., for providing a rearward linear impact force on the anvil 130), as described in more detail elsewhere herein. In some implementations, the thrown mass 126 may include an initial position (or state) that positions the thrown mass 126 proximate to either the rear end 104 or the front end 102 of the orthopedic impactor tool 100 (e.g., which readies the thrown mass 126 to be used to provide either a forward linear impact or a rearward linear impact as described in more detail elsewhere herein).

The reverse impact rods 138 are operatively coupled to the anvil 130. The reverse impact rods 138 limit and guide a range of motion of the thrown mass 126 (e.g., as the thrown mass 126 moves linearly along with the lead nut 122). The anvil 130, the anvil anti-rotation element 132, the forward impact surface 134, the rearward impact surface 136, the reverse impact rods 138, and the anvil guide bushing 140 may form an output anvil assembly that is provided within the enclosure 152. The anvil 130 may be aligned, via the anvil anti-rotation element 132, such that the forward impact surface 134 faces the forward striking surface 128a of the thrown mass 126 and the rearward impact surface 136 faces the rearward striking surface 128b of the thrown mass 126. The anvil 130 is fixedly connected to the reverse impact rods 138 (e.g., which is fixedly connected to the rearward impact surface 136), and the anvil guide bushing 140 guides the anvil 130 during movement of the anvil 130 (e.g., in the forward direction and the rearward direction).

In some implementations, the reverse impact rods 138 may communicate a rearward impact to the anvil 130. Additionally, or alternatively, the reverse impact rods 138 may guide the thrown mass 126 along a linear path with guide bushings 164 (e.g., without rotating when driven by the lead screw 120). In some implementations, the reverse impact rods 138 may be mechanically coupled to the anvil 130 (e.g., fixedly attached to the anvil 130) and may include bearings (and/or a different friction reducing component and/or a motion supporting component, among other examples) enabling linear motion of the thrown mass 126. Additionally, or alternatively, the reverse impact rods 138 may be mechanically coupled to the orthopedic impactor tool 100 (e.g., to the enclosure 152 of the orthopedic impactor tool 100 via alignment bearings 166 proximate the rear end 104 of the orthopedic impactor tool 100, among other examples).

Accordingly, the forward striking surface 128a of the thrown mass 126 may be used to impact the forward impact surface 134 of the anvil 130 (e.g., imparting a forward linear impact force on the anvil 130), and the rearward striking surface 128b of the thrown mass 126 may be used to impact the rearward impact surface 136 of the anvil 130 (e.g., imparting a rearward linear impact force on the anvil 130), as described in more detail elsewhere herein. As an example, the thrown mass 126 may accelerate in the forward direction to cause the forward striking surface 128a of the thrown mass 126 to impact the forward impact surface 134 of the anvil 130. As another example, the thrown mass 126 may accelerate in the rearward direction to cause the rearward striking surface 128b of the thrown mass 126 to impact the rearward impact surface 136 of the anvil 130.

The anvil 130 (and/or the output anvil assembly) is disposed within the enclosure 152 at an initial position. The anvil 130 is moveable in the rearward direction away from the initial position (e.g., toward the rear end 104 of the orthopedic impactor tool 100) and a forward direction toward the initial position (e.g., toward the front end 102 of the orthopedic impactor tool 100). In some implementations, the first sensor 142 may detect that the anvil 130 is positioned in the rearward direction (e.g., toward the rear end 104 of the orthopedic impactor tool 100) and/or may detect that the anvil 130 is positioned in the forward direction (e.g., toward the front end 102 of the orthopedic impactor tool 100). Accordingly, the first sensor 142 may be a position sensor that detects one or more positions of the anvil 130. In some implementations, the anvil 130 may include a biasing element (e.g., shown as a spring 130a in FIG. 1F) which predisposes the anvil 130 to be in a position, such as a position proximate the front end 102 or the rear end 104 of the orthopedic impactor tool 100, among other examples.

As an example, a user of the orthopedic impactor tool 100 may provide a pushing force on the orthopedic impactor tool 100 (e.g., by pushing on the handle 148 of the orthopedic impactor tool 100) that causes the anvil 130 to move in the rearward direction. The first sensor 142 detects that the anvil 130 is being pushed in the rearward direction. The first sensor 142 sends, and the controller 154 receives, sensor input indicating that the anvil 130 is towards the rearward direction.

Based on the anvil 130 being towards the rearward direction, the controller 154 may poll a trigger input of the trigger mechanism 150 to determine whether a trigger input is being provided. The controller 154 may cause, based on determining that the trigger input is being provided, the motor 106 to generate the forward rotational motion that drives the lead screw 120 (e.g., the forward rotational motion generated by the motor 106 causes forward rotational acceleration of the lead screw 120). The forward rotational acceleration of the lead screw 120 causes the lead nut 122 (e.g., which is fixedly attached to the thrown mass 126) to linearly accelerate along the shaft of the lead screw 120 in the forward direction. The thrown mass 126, which is fixedly connected to the lead nut 122, linearly accelerates with the lead nut 122 in the forward direction and the forward striking surface 128a of the thrown mass 126 impacts the forward impact surface 134 of the anvil 130 imparting a forward linear impact force on the anvil 130.

In some implementations, the controller 154 may cause the motor 106 to stop generating the forward rotational motion (e.g., by deactivating the motor 106) that drives the lead screw 120 at, or around, a time that the forward striking surface 128a of the thrown mass 126 impacts the forward impact surface 134 of the anvil 130. As an example, the controller 154 may deactivate the motor 106 before the impact between the forward striking surface 128a of the thrown mass 126 and the forward impact surface 134 of the anvil 130 occurs. This deactivation of the motor is also referred to herein as "coasting the motor" or simply "coasting." As another example, the controller 154 may coast the motor 106 within approximately 50 milliseconds after the impact between the forward striking surface 128a of the thrown mass 126 and the forward impact surface 134 of the anvil 130.

Additionally, or alternatively, the controller 154 may cause power being supplied to the motor 106 to be reduced, which reduces an amount of forward rotational motion (e.g., generated by the motor 106) that drives the lead screw 120 at, or around, a time that the forward striking surface 128a of the thrown mass 126 impacts the forward impact surface 134 of the anvil 130. As an example, the controller 154 may cause power being supplied to the motor 106 to be reduced before the impact between the forward striking surface 128a of the thrown mass 126 and the forward impact surface 134 of the anvil 130 occurs. As another example, the controller 154 may cause power being supplied to the motor 106 to be reduced within approximately 50 milliseconds after the impact between the forward striking surface 128a of the thrown mass 126 and the forward impact surface 134 of the anvil 130.

By limiting the time that the motor 106 is powered, and/or by reducing power being supplied to the motor 106) (e.g., at, or around, a time of impact between the forward striking surface 128a of the thrown mass 126 and the forward impact surface 134 of the anvil 130), it was unexpectedly discovered that the operation and reliability of the orthopedic impactor tool 100 was improved. The operation of the orthopedic impactor tool 100 was improved because a user using the orthopedic impactor tool 100 does not experience a push back as a result of the linear motion converter pushing the anvil 130 against a worksite (e.g., a surgical site). Furthermore, the reliability of the orthopedic impactor tool 100 was improved because the lead screw 120 and the lead nut 122 did not lock up as they did when the motor 106 is continuously powered through the anvil 130 (e.g., if the motor 106 was not deactivated or operated at a reduced power). An additional benefit of the reduced recoil (or push back) is that it is less likely to interfere with robotic guidance and navigation when used for robotic surgery.

In some implementations, the second sensor 144 (e.g., shown as being provided proximate the forward impact surface 134 and along the shaft of the lead screw 120) may detect that the thrown mass 126 has reached a position along the shaft of the lead screw 120. The second sensor 144 may send, and the controller 154 may receive, sensor information indicating that the thrown mass 126 has reached the position along the shaft of the lead screw 120. Based on the sensor information, the controller 154 may reduce or remove power to the motor 106 to stop or reduce generating the forward rotational motion of the linear motion converter (e.g., the lead screw 120).

In some implementations, the controller 154 may cause the motor 106 to stop generating the forward rotational motion (e.g., by removing power from being provided to the motor 106) that drives the lead screw 120 based on a number of revolutions of the lead screw 120. As an example, the controller 154 may infer a linear position of the thrown mass 126 based on the number of revolutions of the lead screw 120. The controller 154 may determine the number of revolutions of the lead screw 120 in any suitable manner, such as via internal sensors of the motor 106, among other examples. In this way, the controller 154 may cause the motor to stop generating the forward rotational motion after a set number of revolutions of the lead screw 120 has occurred (e.g., which corresponds to a particular linear position of the thrown mass 126).

After the forward striking surface 128a of the thrown mass 126 impacts the forward impact surface 134 of the anvil 130, the controller 154 may cause the motor 106 to generate the reverse rotational motion that causes the lead screw 120 to rotate in the reverse direction, which, in turn, causes the lead nut 122 to move linearly along a shaft of the lead screw 120 in the rearward direction to return the thrown mass 126 to the initial state (e.g., which readies the thrown mass 126 to be used to provide another forward linear impact force on the anvil 130).

As another example, the surgeon may provide a pulling force on the orthopedic impactor tool 100 (e.g., by pulling on the handle 148 of the orthopedic impactor tool 100) that causes the anvil 130 to move in the forward direction (e.g., to the initial position). The first sensor 142 detects that the anvil 130 is being pulled in the forward direction (e.g., toward the front end 102 of the orthopedic impactor tool 100). The first sensor 142 sends, and the controller 154 receives, sensor input indicating that the anvil 130 is towards the forward direction.

Based on the anvil 130 being towards the forward direction, the controller 154 may poll a trigger input of the trigger mechanism 150 to determine whether a trigger input is being provided. The controller 154 may determine (e.g., based on data obtained by the second sensor 144) whether the thrown mass 126 is in a position proximate the front end 102 of the orthopedic impactor tool 100 and ready to be used to provide a rearward linear impact force).

Based on determining that the thrown mass 126 is not in the rearward impact position, the controller 154 may cause the motor 106 to generate the forward rotational motion that causes the lead screw 120, and, in turn, the lead nut 122 to move linearly in the forward direction until the lead nut 122 positions the thrown mass 126 in the rearward impact position.

Based on determining that the thrown mass 126 is in the rearward impact position the controller 154 may cause the motor 106 to generate the reverse rotational motion that drives the lead screw 120 (e.g., the reverse rotational motion generated by the motor 106 causes reverse rotational acceleration of the lead screw 120). The reverse rotational acceleration of the lead screw 120 causes the lead nut 122 (e.g., which is fixedly attached to the thrown mass 126) to linearly accelerate along the shaft of the lead screw 120 in the rearward direction. The thrown mass 126, which is fixedly connected to the lead nut 122, linearly accelerates with the lead nut 122 in the rearward direction and the rearward striking surface 128b of the thrown mass 126 impacts the rearward impact surface 136 of the anvil 130 imparting a rearward linear impact force on the anvil 130.

In some implementations, the controller 154 may cause the motor 106 to stop generating the reverse rotational motion (e.g., by deactivating the motor 106) that drives the lead screw 120 at, or around, a time that the forward striking surface 128a of the thrown mass 126 impacts the rearward impact surface 136 of the anvil 130 (e.g., in a same or similar manner as the controller 154 causes the motor 106 to stop generating the forward rotational motion, as described in more detail elsewhere herein. As an example, the controller 154 may deactivate the motor 106 before the impact between the forward striking surface 128a of the thrown mass 126 impacts the rearward impact surface 136 of the anvil 130 occurs. As another example, the controller 154 may deactivate the motor 106 within approximately 50 milliseconds after the impact between the forward striking surface 128a of the thrown mass 126 impacts the rearward impact surface 136 of the anvil 130. Limiting the time that the motor 106 is powered before a rearward impact has the same, or similar, benefits as limiting the time that the motor 106 is powered before a forward impact, as described in more detail elsewhere herein.

After the rearward striking surface 128b of the thrown mass 126 impacts the rearward impact surface 136 of the reverse impact rods 138, the controller 154 may cause the motor 106 to generate a rotational motion that causes the lead screw 120 to rotate which, in turn, causes the lead nut 122 to move linearly along a shaft of the lead screw 120 in a direction to return the thrown mass 126 to an initial state.

In some implementations, a detent (e.g., shown as a detent element 156), such as a magnet, among other examples, holds (or retains) the thrown mass 126 in a position at either end of a stroke. It was unexpectedly discovered that without the detent, the thrown mass (e.g., the thrown mass 126) may remain between ends of the drive stroke and, as a result, the thrown mass would have less time to accelerate yielding a lower than desired impact energy.

In some implementations, the orthopedic impactor tool 100 uses the one or more impact absorbing mechanisms (e.g., a first impact absorbing mechanism 158 and/or a second impact absorbing mechanism 160) because it was unexpectedly discovered that, without having the one or more impact absorbing mechanisms positioned to absorb impact energy communicated from the thrown mass 126 to the orthopedic impactor tool 100 during an operational cycle (e.g., during the drive stroke and/or the return stroke), the unabated impact forces may cause the orthopedic impactor tool 100 to lock up and be damaged. This is especially true if the orthopedic impactor tool 100 was cycled with minimal resistance to anvil movement, such as what might occur if the orthopedic impactor tool 100 tool was cycled without having a surgical implement attached, for example.

As described herein, an "anvil stroke" is a stroke that the anvil 130 may move prior to the anvil 130 contacting an impact absorbing mechanism (e.g., the first impact absorbing mechanism 158 and/or the second impact absorbing mechanism 160, among other examples). In other words, the anvil stroke of the anvil 130 is an amount of free movement between a first anvil position (e.g., a forward position where the anvil 130 is located proximate the first impact absorbing mechanism 158) and a second anvil position (e.g., a rearward position where the anvil 130 is located proximate the second impact absorbing mechanism 160).

Upon implementing the one or more impact absorbing mechanisms (e.g., by using end of stroke bumpers, among other examples), it was further unexpectedly discovered that a bumper material may be optimized (e.g., with regards to one or more properties of the bumper material, among other examples) to provide one or more benefits associated with the orthopedic impactor tool 100. For example, the orthopedic impactor tool 100 may use a material (e.g., a highly dampening urethane material, among other examples) for the one or more impact absorbing mechanisms. These materials may be characterized by a rebound (e.g., a rebound of less than 50% or a rebound of less than 30%, among other examples) that enhances an experience of the user of the orthopedic impactor tool 100. As an example, not only did it reduce vibrations associated with the orthopedic impactor tool 100, but it also significantly reduced noise associated with the orthopedic impactor tool 100. This unexpected reduction in noise is a significant benefit in that a typical worksite (e.g., an operating room) has poor acoustics and users (e.g., surgeons operating in the operating room) often complain that typical tools (e.g., typical powered and/or non-powered impactor tools) create high noise levels (e.g., often exceeding 95 decibels (dB)). The selection of dampening (e.g., highly dampening) materials for the one or more impact absorbing mechanisms (e.g., the materials for the end of stroke bumpers) significantly reduces the noise level. Although low rebound materials are provided as examples, other materials, such as composites with less than a 30% rebound, may be used to provide a damped system (e.g., a critically damped system including the thrown mass 126 impacting the end of stroke bumper) and accomplish a similar result.

In some implementations, an impact frequency parameter (e.g., associated with a number of impacts or cycles per second, among other examples) of the orthopedic impactor tool 100 and/or a time constant parameter of the one or more impact absorbing mechanisms (e.g., which characterizes a time-dependent behavior of a deformation and recovery of a material of the one or more impact absorbing mechanisms) may be optimized such that the time constant is less than 50% of a time of the operational cycle of the orthopedic impactor tool 100. In this way, the material of the one or more impact absorbing mechanisms may recover to at least 90% of an original state within approximately two time constants, which improves an experience of the surgeon by minimizing vibrations and maintaining consistent performance. In some implementations, the first impact absorbing mechanism 158, which may also be referred to herein as a forward impact bumper, and the second impact absorbing mechanism 160, which may also be referred to herein as a rearward impact bumper, may absorb impact energy associated with operation of the orthopedic impactor tool 100. The first impact absorbing mechanism 158 is disposed on the orthopedic impactor tool 100 proximate the front end 102 of the orthopedic impactor tool 100 to absorb impact energy associated with a forward contact caused by the thrown mass 126 (e.g., based on a drive stroke and/or the return stroke). The first impact absorbing mechanism 158 is disposed on the orthopedic impactor tool 100 proximate the rear end 104 to absorb impact energy associated with a rearward contact caused by the thrown mass 126 (e.g., based on the drive stroke and/or the return stroke).

It was unexpectedly discovered that, while using the orthopedic impactor tool 100 with the end of stroke bumpers and limiting an anvil stroke of the anvil 130 to less than 6 mm, the orthopedic impactor tool 100 may be used for controlled precise impacting with osteotomes. This substantially expanded the usefulness of the orthopedic impactor tool 100 compared to other surgical power impacting tools which have anvil strokes in excess of 10 mm and are uncontrolled when trying to precisely use osteotomes in a surgical attachment to the impactor. In some implementations, the operational cycle of the orthopedic impactor tool 100 may represent a first impact in a first direction (e.g., a desired impact direction or a primary direction) and a second impact in a second direction (e.g., a return direction) before returning to the initial position. It was unexpectedly discovered that continuous bidirectional impacting in this manner (e.g., in which impacts occur in both a forward and a rearward direction) resulted in efficient cutting and removal of material from a bone cavity and faster shaping of the bone cavity for a prosthesis compared to typical impacting techniques. It was further discovered that, in some implementations, limiting the anvil stroke when operating in this mode to between approximately 3 mm to 8 mm minimized a jackhammer effect associated with operating the orthopedic impactor tool 100 in a bidirectional mode. In some implementations, the anvil stroke may be less than 8 mm but greater than the pitch of the cutting teeth of the surgical instrument 168.

The controller 154 may modulate one or more parameters related to the motor 106 (e.g., a power of the motor 106 and/or a speed of the motor 106, among other examples) before and/or during the drive stroke and/or the return stroke to control an impact energy of the thrown mass 126.

For example, the controller 154 may modulate the power of the motor 106 such that the impact energy in the first drive direction is a first value and the impact energy in the second direction is a second value that is a same value as the first value or a different value than the first value. As an example, the controller 154 may modulate the power of the motor 106 during the return stroke (e.g., during reset of the thrown mass 126 to the initial position prior to a next drive stroke) to significantly reduce the impact energy of the thrown mass 126 as it returns from the desired impact direction such that the impact in the second direction is less than a percentage of the impact energy as a result of the impact in the desired impact direction (e.g., less than 30% of the impact energy of the desired direction, among other examples).

As another example, the controller 154 may modulate the speed of the motor 106 during the drive stroke to control the impact energy of the thrown mass 126. As an example, the orthopedic impactor tool 100 may use the one or more sensors (e.g., the first sensor 142, the second sensor 144, and/or the third sensor 146) and the controller 154 to register a position of the thrown mass 126. Based on registering the position of the thrown mass 126, the controller 154 causes (e.g., via modulation of the motor 106) the impact energy of the thrown mass 126 to be a percentage (e.g., less than 20%, among other examples) of a maximum impact energy of the thrown mass 126 before the thrown mass 126 engages the first impact absorbing mechanism 158 (e.g., after an impact in the forward direction) or the first impact absorbing mechanism 158 (e.g., after an impact in the rearward direction).

Additionally, or alternatively, the controller 154 may modulate the power of the motor 106 before a start of the operational cycle to control the impact energy during the operational cycle. As an example, if a patient is osteoporotic, the controller 154 may modulate the power of the motor 106 to provide low energy impacts rather than high energy impacts which could damage a bone of the patient.

Accordingly, the orthopedic impactor tool 100 of the present disclosure communicates energy necessary to provide high energy linear impacts more efficiently, and has an increased robustness, compared to typical powered impactor tools, as described in more detail elsewhere herein. Additionally, because the orthopedic impactor tool 100 uses a drive axis (e.g., the drive axis X1) and an impact axis (e.g., the impact axis X2) that are independent from one another (e.g., that operate on independent axes), a length of the orthopedic impactor tool 100 is substantially reduced compared to a length of typical powered impactor tools and reactionary shock associated with linear impacts to the motor 106 is significantly reduced as it is no longer transmitted along a single axis.

As indicated above, FIGS. 1A-1G are provided as examples. Other examples may differ from what is described with regard to FIGS. 1A-1G. The number and arrangement of the various components shown in FIGS. 1A-1G are provided as examples. In practice, there may be additional components, fewer components, different components, or differently arranged components than those shown in FIGS. 1A-1G. Additionally, or alternatively, a set of components (e.g., one or more components) shown in FIGS. 1A-1G may perform one or more functions described as being performed by another set of components shown in FIGS. 1A-1G.

Figure 2:
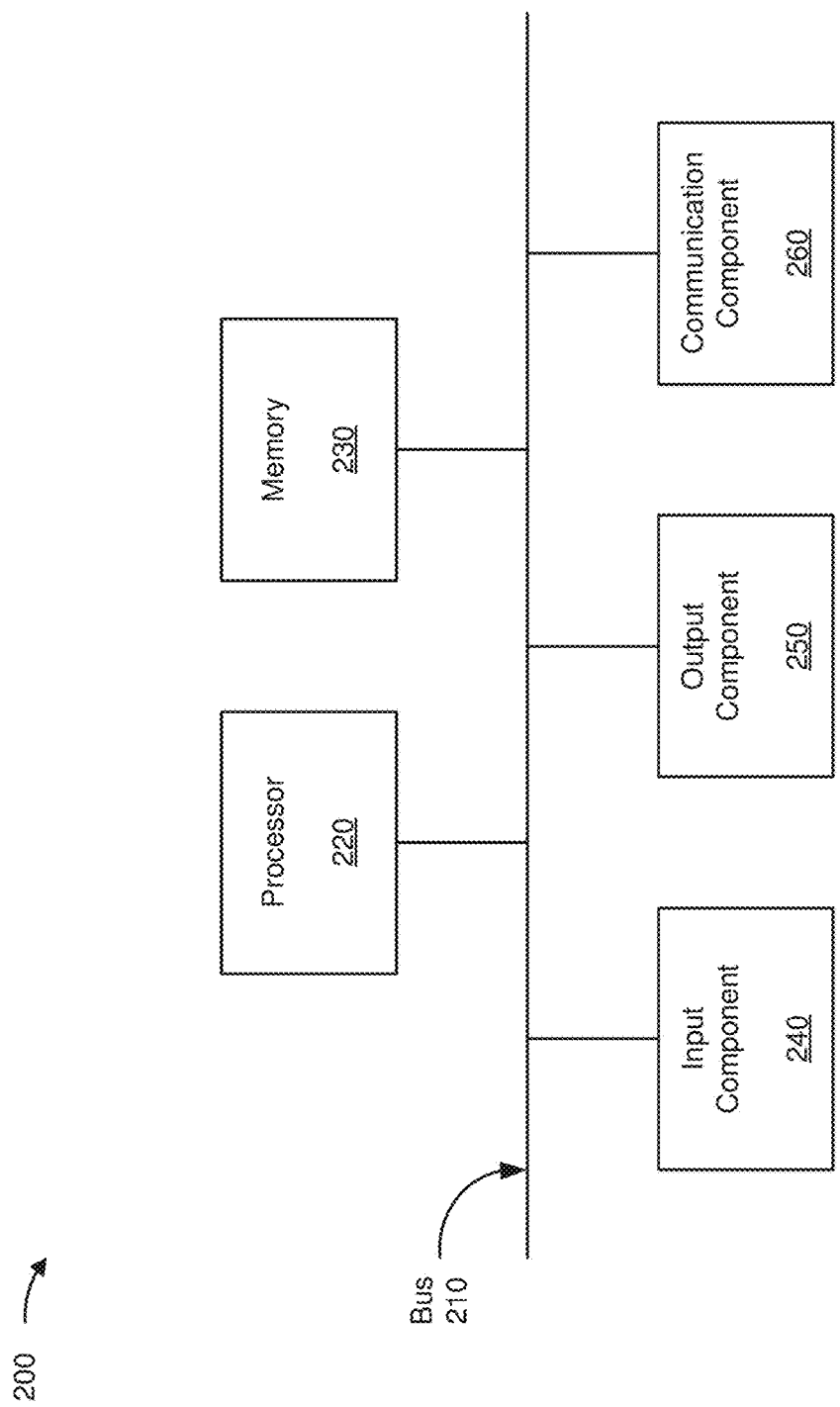
FIG. 2 is a diagram of example components of a device associated with an orthopedic impactor tool, in accordance with some embodiments of the present disclosure.

FIG. 2 is a diagram of example components of a device associated with an improved orthopedic impactor tool (e.g., the orthopedic impactor tool 100 of FIGS. 1A-1G). The device 200 may correspond to one or more components of the orthopedic impactor tool 100 (e.g., the controller 154). In some implementations, one or more components of the orthopedic impactor tool 100 (e.g., the controller 154) may include one or more of the devices 200 and/or one or more components of the device 200. As shown in FIG. 2, the device 200 may include a bus 210, a processor 220, a memory 230, an input component 240, an output component 250, and/or a communication component 260.

The bus 210 may include one or more components that enable wired and/or wireless communication among the components of the device 200. The bus 210 may couple together two or more components of FIG. 2, such as via operative coupling, communicative coupling, electronic coupling, and/or electric coupling. For example, the bus 210 may include an electrical connection (e.g., a wire, a trace, and/or a lead) and/or a wireless bus. The processor 220 may include a central processing unit, a graphics processing unit, a microprocessor, a controller, a microcontroller, a digital signal processor, a field-programmable gate array, an application-specific integrated circuit, and/or another type of processing component. The processor 220 may be implemented in hardware, firmware, or a combination of hardware and software. In some implementations, the processor 220 may include one or more processors capable of being programmed to perform one or more operations or processes described elsewhere herein.

The memory 230 may include volatile and/or nonvolatile memory. For example, the memory 230 may include random access memory (RAM), read only memory (ROM), a hard disk drive, and/or another type of memory (e.g., a flash memory, a magnetic memory, and/or an optical memory). The memory 230 may include internal memory (e.g., RAM, ROM, or a hard disk drive) and/or removable memory (e.g., removable via a universal serial bus connection). The memory 230 may be a non-transitory computer-readable medium. The memory 230 may store information, one or more instructions, and/or software (e.g., one or more software applications) related to the operation of the device 200. In some implementations, the memory 230 may include one or more memories that are coupled (e.g., communicatively coupled) to one or more processors (e.g., processor 220), such as via the bus 210. Communicative coupling between a processor 220 and a memory 230 may enable the processor 220 to read and/or process information stored in the memory 230 and/or to store information in the memory 230.

The input component 240 may enable the device 200 to receive input, such as user input and/or sensed input. For example, the input component 240 may include a touch screen, a keyboard, a keypad, a mouse, a button, a microphone, a switch, a sensor, a global positioning system sensor, a global navigation satellite system sensor, an accelerometer, a gyroscope, and/or an actuator. The output component 250 may enable the device 200 to provide output, such as via a display, a speaker, and/or a light-emitting diode. The communication component 260 may enable the device 200 to communicate with other devices via a wired connection and/or a wireless connection. For example, the communication component 260 may include a receiver, a transmitter, a transceiver, a modem, a network interface card, and/or an antenna.

The device 200 may perform one or more operations or processes described herein. For example, a non-transitory computer-readable medium (e.g., memory 230) may store a set of instructions (e.g., one or more instructions or code) for execution by the processor 220. The processor 220 may execute the set of instructions to perform one or more operations or processes described herein. In some implementations, execution of the set of instructions, by one or more of the processors 220, causes the one or more of the processors 220 and/or the device 200 to perform one or more operations or processes described herein. In some implementations, hardwired circuitry may be used instead of or in combination with the instructions to perform one or more operations or processes described herein. Additionally, or alternatively, the processor 220 may be configured to perform one or more operations or processes described herein. Thus, implementations described herein are not limited to any specific combination of hardware circuitry and software.

The number and arrangement of components shown in FIG. 2 are provided as an example. The device 200 may include additional components, fewer components, different components, or differently arranged components than those shown in FIG. 2. Additionally, or alternatively, a set of components (e.g., one or more components) of the device 200 may perform one or more functions described as being performed by another set of components of the device 200.

Figure 3:
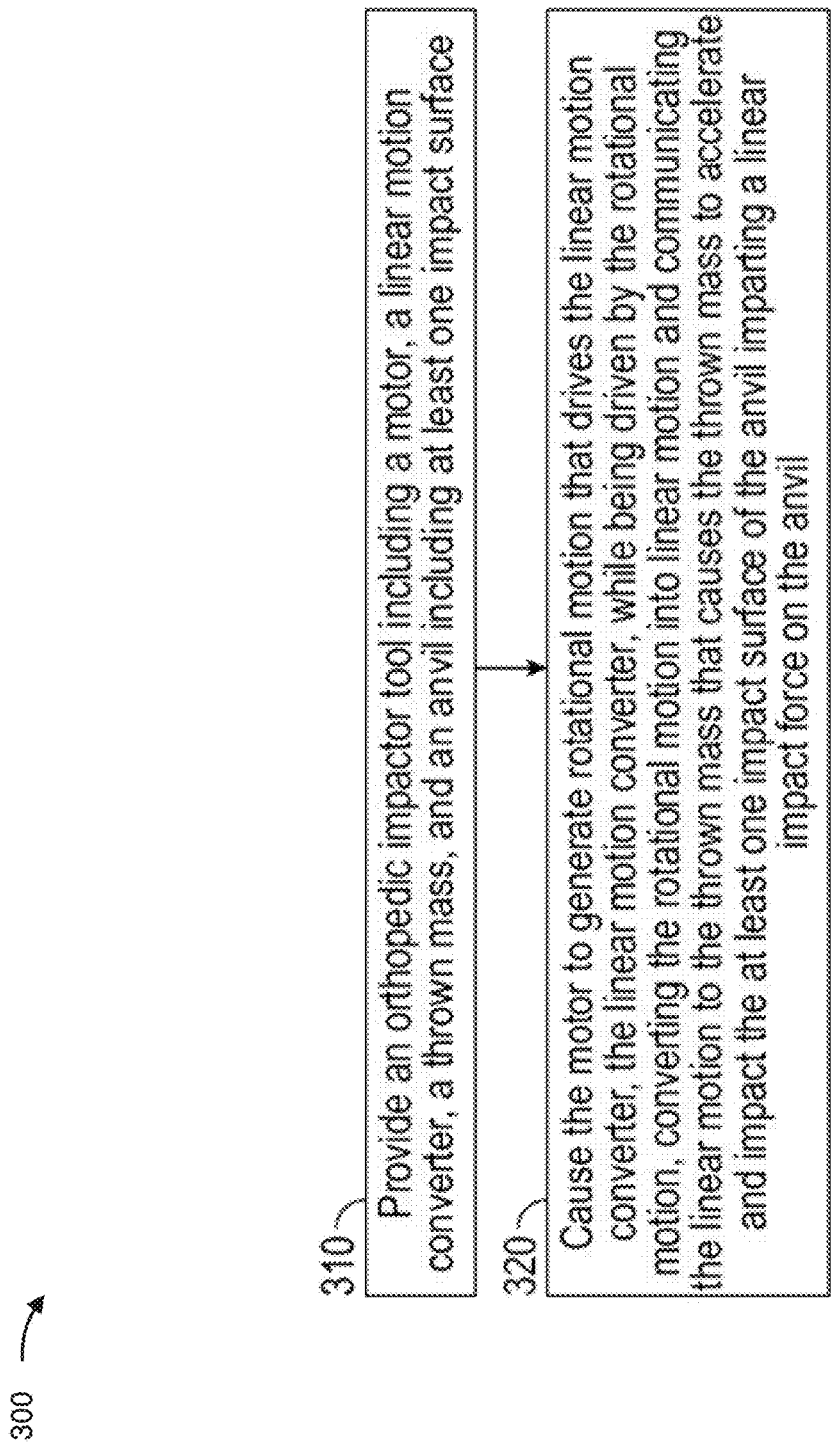
FIG. 3 is a flowchart of an example process associated with operating an orthopedic impactor tool, in accordance, in accordance with some embodiments of the present disclosure.

FIG. 3 is a flowchart of an example process 300 associated with operating an orthopedic impactor tool. As shown in FIG. 3, the process 300 includes providing an orthopedic impactor tool including a motor, a linear motion converter, a thrown mass, and an anvil including at least one impact surface (block 310). In some implementations, the motor and the linear motion converter operate on independent axes.

As further shown in FIG. 3, the process 300 includes causing (e.g., by a controller) the motor to generate rotational motion that drives the linear motion converter, the linear motion converter, while being driven by the rotational motion, converting the rotational motion into linear motion and communicating the linear motion to the thrown mass that causes the thrown mass to accelerate and impact the at least one impact surface of the anvil imparting a linear impact force on the anvil (block 320).

In some implementations, the process 300 may include causing (e.g., by the controller) the motor to stop generating the rotational motion that drives the linear motion converter before the thrown mass impacts the anvil. The process 300 may include detecting, by the controller, movement of the anvil, and the controller may cause the motor to generate the rotational motion that drives the linear motion converter in response to detecting the movement of the anvil.

Although FIG. 3 shows example blocks of the process 300, in some implementations, the process 300 may include additional blocks, fewer blocks, different blocks, or differently arranged blocks than those depicted in FIG. 3. Additionally, or alternatively, two or more of the blocks of the process 300 may be performed in parallel. The process 300 is an example of one process that may be performed by one or more devices described herein. These one or more devices may perform one or more other processes based on operations described herein, such as the operations described in connection with FIGS. 1A-1G. Moreover, while the process 300 has been described in relation to the devices and components of the preceding figures, the process 300 can be performed using alternative, additional, or fewer devices and/or components. Thus, the process 300 is not limited to being performed with the example devices, components, hardware, and software explicitly enumerated in the preceding figures.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An orthopedic impactor tool, comprising:
a motor;
a linear motion converter operatively coupled to the motor;
a thrown mass operatively coupled to the linear motion converter; and
an anvil including at least one impact surface;
wherein, during an operational cycle of the orthopedic impactor tool, the motor generates rotational motion that drives the linear motion converter,
wherein the linear motion converter, while being driven by the rotational motion, converts the rotational motion into linear motion and communicates the linear motion to the thrown mass,
wherein the linear motion, communicated to the thrown mass, causes the thrown mass to accelerate and impact the at least one impact surface imparting a linear impact force on the anvil,
wherein the motor and the linear motion converter operate on independent axes, and
wherein an anvil stroke is limited to less than 8 millimeters before the thrown mass impacts a bumper.

2. The orthopedic impactor tool of claim 1, further comprising:
a surgical instrument, operatively coupled to the anvil, including cutting teeth,
wherein the cutting teeth are spaced apart by a pitch, and
wherein an anvil stroke is less than 8 millimeters but greater than the pitch.

3. The orthopedic impactor tool of claim 1, wherein, during the operational cycle, the motor at least one of coasts, or operates at reduced power, for a time period before the thrown mass impacts the at least one impact surface.

4. The orthopedic impactor tool of claim 1, further comprising:
a detent element that retains the thrown mass in a position at an end of a return stroke.

5. The orthopedic impactor tool of claim 1, wherein the operational cycle represents a first impact in a first direction and a second impact in a second direction before returning an initial position, and
wherein an impact energy in the first direction is a first value, and
wherein an impact energy in the second direction is a second value that is less than 30% of the first value.

6. The orthopedic impactor tool of claim 1, further comprising:
an axial support mechanism that decouples the motor from the linear motion converter during one or more impacts caused by the thrown mass.

7. The orthopedic impactor tool of claim 1, further comprising:
an impact absorbing mechanism that absorbs at least a portion of impact energy caused by the thrown mass.

8. An orthopedic impactor tool, comprising:
a motor;
a linear motion converter operatively coupled to the motor;
a thrown mass operatively coupled to the linear motion converter; and
an anvil including at least one impact surface;
wherein, during an operational cycle of the orthopedic impactor tool, the motor generates rotational motion that drives the linear motion converter,
wherein the linear motion converter, while being driven by the rotational motion, converts the rotational motion into linear motion and communicates the linear motion to the thrown mass,
wherein the linear motion, communicated to the thrown mass, causes the thrown mass to accelerate towards the at least one impact surface of the anvil,
wherein the motor at least one of coasts, or operates a reduced motor power, before the thrown mass imparts a linear impact on the at least one impact surface of the anvil, and
wherein the linear motion converter is operatively coupled to the motor via an elastic member that slips based on a threshold slip torque.

9. The orthopedic impactor tool of claim 8, wherein the motor and the linear motion converter operate on independent axes.

10. The orthopedic impactor tool of claim 8, further comprising:
a detent element that retains the thrown mass in a position at an end of a return stroke.

11. The orthopedic impactor tool of claim 8, wherein an impact energy of the thrown mass is reduced to a percentage of a maximum impact energy of the thrown mass before the thrown mass impacts the at least one impact surface.

12. The orthopedic impactor tool of claim 8, further comprising:
an axial decoupling mechanism that substantially isolates the motor from impact forces generated during one or more impacts of the thrown mass.

13. The orthopedic impactor tool of claim 8, further comprising:
an impact absorbing mechanism that absorbs at least a portion of impact energy caused by the thrown mass.

14. The orthopedic impactor tool of claim 8, further comprising:
a detent element that retains the thrown mass in a position at an end of a return stroke.

15. An orthopedic impactor tool, comprising:
a motor;
a linear motion converter operatively coupled to the motor;
a thrown mass operatively coupled to the linear motion converter;
an anvil including at least one impact surface;
wherein, during an operational cycle of the orthopedic impactor tool, the motor generates rotational motion that drives the linear motion converter,
wherein the linear motion converter, while being driven by the rotational motion, converts the rotational motion into linear motion and communicates the linear motion to the thrown mass,
wherein the linear motion, communicated to the thrown mass, causes the thrown mass to accelerate towards the at least one impact surface of the anvil, and
wherein the motor at least one of coasts, or operates a reduced motor power, before the thrown mass imparts a linear impact on the at least one impact surface of the anvil; and
a surgical instrument, operatively coupled to the anvil, including cutting teeth,
wherein the cutting teeth are spaced apart by a pitch, and
wherein an anvil stroke is less than 8 millimeters but greater than the pitch.

16. The orthopedic impactor tool of claim 15, wherein the motor and the linear motion converter operate on independent axes.

17. The orthopedic impactor tool of claim 15, wherein an impact energy of the thrown mass is reduced to a percentage of a maximum impact energy of the thrown mass before the thrown mass impacts the at least one impact surface.

18. The orthopedic impactor tool of claim 15, further comprising:
   an axial decoupling mechanism that substantially isolates the motor from impact forces generated during one or more impacts of the thrown mass.

19. The orthopedic impactor tool of claim 15, further comprising:
   an impact absorbing mechanism that absorbs at least a portion of impact energy caused by the thrown mass.

\* \* \* \* \*